(12) United States Patent
Stampanoni et al.

(10) Patent No.: US 9,117,296 B2
(45) Date of Patent: Aug. 25, 2015

(54) METHOD FOR IMAGE FUSION BASED ON PRINCIPAL COMPONENT ANALYSIS

(75) Inventors: Marco Stampanoni, Endingen (CH); Zhentian Wang, Villigen (CH)

(73) Assignee: Paul Scherrer Institut, PSI/Villigen (CH)

( * ) Notice: Subject to any disclaimer, the term of this patent is extended or adjusted under 35 U.S.C. 154(b) by 27 days.

(21) Appl. No.: 14/235,570

(22) PCT Filed: Jul. 20, 2012

(86) PCT No.: PCT/EP2012/064306
§ 371 (c)(1),
(2), (4) Date: Feb. 13, 2014

(87) PCT Pub. No.: WO2013/014083
PCT Pub. Date: Jan. 31, 2013

(65) Prior Publication Data
US 2014/0169698 A1 Jun. 19, 2014

(30) Foreign Application Priority Data

Jul. 28, 2011 (EP) .................................. 11175756

(51) Int. Cl.
| | |
|---|---|
| *G06K 9/36* | (2006.01) |
| *G06T 5/50* | (2006.01) |
| *G01N 23/06* | (2006.01) |
| *G06T 11/00* | (2006.01) |
| *A61B 6/00* | (2006.01) |

(52) U.S. Cl.
CPC . *G06T 5/50* (2013.01); *A61B 6/483* (2013.01); *A61B 6/484* (2013.01); *A61B 6/5235* (2013.01); *G01N 23/06* (2013.01); *G06T 11/003* (2013.01); *A61B 6/4035* (2013.01); *A61B 6/4291* (2013.01); *G01N 2223/401* (2013.01)

(58) Field of Classification Search
CPC ....... G06T 5/50; G06T 11/003; G06T 7/0012; G06T 7/0081; G06T 3/4038; G06T 11/60; G01N 21/255; H04N 1/3876; H04N 5/23238
See application file for complete search history.

(56) References Cited

U.S. PATENT DOCUMENTS

| | | | |
|---|---|---|---|
| 8,041,004 B2 | 10/2011 | David et al. | |
| 8,417,060 B2 * | 4/2013 | Abousleman et al. | ........ 382/284 |

(Continued)

FOREIGN PATENT DOCUMENTS

| | | |
|---|---|---|
| EP | 1879020 A1 | 1/2008 |
| EP | 2585817 A1 | 5/2013 |

(Continued)

*Primary Examiner* — Amir Alavi
(74) *Attorney, Agent, or Firm* — Laurence A. Greenberg; Werner H. Stemer; Ralph E. Locher

(57) ABSTRACT

An image fusion method combines absorption, differential phase contrast and dark-field (scattering) signals obtained with X-ray phase contrast sensitive techniques, such as an arrangement of gratings. The process fuses the absorption and dark-field signals by principal component analysis. Further the differential phase contrast is merged into the PCA fused image to obtain an edge enhancement effect. Due to its general applicability and its simplicity in usage, the proposed process is usable as a standard method for image fusion scheme using phase contrast imaging, in particular on medical scanners (for instance mammography), inspection at industrial production lines, non-destructive testing, and homeland security.

17 Claims, 2 Drawing Sheets

(56) References Cited

U.S. PATENT DOCUMENTS

| | | |
|---|---|---|
| 8,582,815 B2 * | 11/2013 | Sasaki .......................... 382/103 |
| 2004/0258202 A1 | 12/2004 | Wernick et al. |
| 2007/0086675 A1 * | 4/2007 | Chinen et al. ................ 382/284 |
| 2008/0123975 A1 * | 5/2008 | Otsu et al. .................... 382/236 |
| 2012/0041679 A1 | 2/2012 | Stampanoni et al. |
| 2014/0169698 A1 * | 6/2014 | Stampanoni et al. ......... 382/284 |
| 2014/0355824 A1 * | 12/2014 | Iwasaki ......................... 382/103 |

FOREIGN PATENT DOCUMENTS

| | | |
|---|---|---|
| WO | 2010089319 A1 | 8/2010 |
| WO | 2012000694 A1 | 1/2012 |

* cited by examiner

METHOD FOR IMAGE FUSION BASED ON PRINCIPAL COMPONENT ANALYSIS

This application is a 371 of PCT/EP2012/064306 filed on Jul. 20, 2012

BACKGROUND OF THE INVENTION

Field of the Invention

The present invention relates to a method for image fusion based on Principal Component Analysis (PCA) for differential phase contrast imaging merging the absorption (AC), differential phase (DPC) and dark-field (DFI) signals It is well known that, differently from conventional visible light optics, the refractive index in X-ray optics is very close to and smaller than unity. In first approximation, for small and negligible anisotropy in the medium, the index of refraction characterizing the optical properties of a tissue can be expressed—including X-ray absorption—with its complex form:

$$n = 1 - \delta - i\beta,$$

where $\delta$ is the decrement of the real part of the refractive index, characterizing the phase shifting property, while the imaginary part $\beta$ describes the absorption property of the sample. In conventional absorption-based radiography, the X-ray phase shift information is usually not directly utilized for image reconstruction. However, at photon energies greater than 10 keV and for light materials (made up of low-Z elements), the phase shift term plays a more prominent role than the attenuation term because $\delta$ is typically three orders of magnitude larger than $\beta$. As a consequence, phase-contrast modalities can generate significantly greater image contrast compared to conventional, absorption-based imaging. Furthermore, far from absorption edges, $\delta$ is inversely proportional to the square of the X-ray energy whilst $\beta$ decreases as the fourth power of energy. A significant consequence of this mechanism is that phase signals can be obtained with much lower dose deposition than absorption, a very important issue when radiation damage has to be taken into account such as in biological samples or in living systems.

Several approaches have been developed in order to record the phase signal. They can be classified as interferometric methods (with crystals), phase propagation methods, techniques based on an analyzer crystal, or on x-ray gratings. The described invention is in context with any of the aforementioned techniques, provided absorption, differential phase and dark-field signals are accessible as details in the case of grating interferometry are given in the European Patent Application EP 10 167 569 and the International Patent Application WO 2010/089319.

X-Ray Imaging Based on Gratings

Grating-based x-ray imaging setups can simultaneously generate three different signals: the conventional absorption contrast (AC) signal, the differential phase contrast (DPC) signal caused by refraction [1], and the so-called dark-field image (DFI) contrast signal cased by scattering on in-homogeneities in the sample [2]. The DPC image signal can be used to obtain phase contrast (PC) images by image processing routines [3, 4]. Set-ups with two gratings (G1 and G2) or three gratings (G0, G1, and G2) can be applied to record the deflection of the x-rays.

In the case of a two-grating set-up, the source needs to fulfill certain requirements regarding its spatial coherence, while in a three grating setup no spatial coherence is required [5, 6]. Therefore, the three grating set-up is suited for use with incoherent x-ray sources, in particular with x-ray tubes. FIG. 1 shows a state of the art two-grating set-up (top) and three-grating set-up (bottom) for x-ray imaging. A G0 grating is required, when the source size is bigger than $p2*l/d$, where p2 is the period of G2, l is the distance between the source and G1, and d is the distance between the gratings G1 and G2.

To separate the conventional attenuation contrast (AC) from the DPC and DFI contrast, a phase-stepping approach is usually applied. One of the gratings is displaced transversely to the incident beam whilst acquiring multiple images. The intensity signal at each pixel in the detector plane oscillates as a function of the displacement. The average value of the oscillation represents the attenuation contrast (AC). The phase of the oscillation can be directly linked to the wavefront phase profile and thus to the DPC signal. The amplitude of the oscillation depends on the scattering of x-rays in the object and thus yields the DFI signal.

For the (two or three) gratings, several approaches have been proposed and applied. The grating G0 (if required) is the one closest to the x-ray source. It usually consists of a transmission grating of absorbing lines with the period p0. It can be replaced by a source that emits radiation only from lines with the same period. The grating G1 is placed further downstream of the source. It consists of lines with a period p1. The grating G2 is the one most downstream of the setup. It usually consists of a transmission grating of absorbing lines with the period p2. It can be replaced by a detector system that has a grating-like sensitivity with the same period.

Two regimes of setups can be distinguished: in the so called "near field regime" and the "Talbot regime". In the "near field regime", the grating period p, grating distances d and the x-ray wavelength $\lambda$ are chosen such, that diffraction effects are negligible. In this case, all gratings need to consist of absorbing lines. In the Talbot regime, diffraction on the grating structures is significant. A sharp distinction between the two regimes is not easily given, as the exact criterion depends on the duty cycle of the grating structure, and whether the gratings are absorbing or phase shifting. E.g., for a grating with absorbing lines and a duty cycle of 0.5, the condition for the "near field regime" is $d \geq p2/2\lambda$. Here G1 should consist of grating lines that are either absorbing or, preferentially, phase shifting. Several amounts of phase shift are possible, preferentially $\pi/2$ or multiples thereof. The grating periods must be matched to the relative distances between the gratings. In case of setups in the "Talbot regime" the Talbot effect needs to be taken into account to obtain good contrast. The formulae for the grating periods and distances are described in [8]. The sample is mostly placed between G0 of G1 (or upstream of G1 in case of a two-grating set-up), however it can be advantageous to place it between G1 and G2 [9].

The presented invention is relevant in all of the abovementioned cases, i.e. in the two- and three-grating case, in the case of the "nearfield regime" and the "Talbot regime", and for the sample placed upstream or downstream of G1. In addition, the invention presented here also works in combination with scanning-based systems as suggested in [10, 11] or for planar grating geometries, as suggested in [12].

For each pixel on the detector, absorption (AC), differential phase (DPC) and darkfield (DFI) signals can be calculated knowing mean, phase and visibility of the intensity curve with and without sample [1, 2].

Since the grating based x-ray interferometer records three kinds of signals which are generated by different physical quantities, a rising question is how to effectively fuse these signals into one single image.

BRIEF SUMMARY OF THE INVENTION

It is therefore the object of the present invention to supply a method for such an image fusion in order to integrate complementary as well as redundant information from multiple images into a single output image. For instance, image fusion could play a very important role in nowadays medical imaging. The merged image can leads to additional clinical information, not obviously detectable in the single images, and therefore results in a more accurate diagnosis.

These objectives are achieved according to the present invention by a method for image fusion being based on Principal Component Analysis (PCA) for differential phase contrast imaging merging the absorption (AC), differential phase (DPC) and dark-field (DFI) signals, comprising the steps of:

a) gathering a series of 2D images, each image comprising absorption dominated pixel and/or differential phase dominated pixel and/or dark field dominated signals;

b) obtaining a vector image by the column-wise extraction of pixel values for each of the absorption dominated pixels and the differential phase dominated pixels and the dark field dominated pixels, c) fusing the vector images of the absorption dominated pixels and the dark-field dominated pixels by a principal component analysis (PCA) in order to generate PCA fused images; and d) merging the vector images of the differential phase dominated pixels into the corresponding PCA fused images by either spatial space methods, Fourier space methods or other suitable images fusion schemes, such as PCA.

The present invention therefore supplies a method for the image fusion which integrates complementary as well as redundant information from multiple images into a single output image. The merged image leads to additional clinical information, not obviously detectable in the single images, and therefore results in a more accurate diagnosis.

The method requires the provision of a suitable set-up. The differential data is preferably obtained from an arrangement for x-rays, in particular hard x-rays, for obtaining quantitative x-ray images from a sample comprising:

a) an X-ray source (x-ray);

b) at least a first grating (G1) and a second grating (G2) dubbed;

c) a position-sensitive detector (PSD) with spatially modulated detection sensitivity having a number of individual pixels;

d) means for recording the images of the detector (PSD);

e) means for evaluating the intensities for each pixel in a series of images in order to identify the characteristic of the object for each individual pixel as an absorption dominated pixel and/or a differential phase contrast dominated pixel and/or an x-ray scattering dominated pixel;

f) wherein the series of images is collected by continuously or stepwise rotating from 0 to $\pi$ or $2\pi$ either the sample or the arrangement and the source relative to the sample.

Typically, the images are achieved by the set-up operated either in the near field regime or in the Talbot-regime. Preferably, the first grating is a line grating being designed either as an absorption grating or a phase grating which is a low absorption grating but generating a considerable X-ray phase shift, the latter preferably of $\pi$ or odd multiples thereof.

In a further preferred embodiment of the present invention, the second grating is a line grating having a high X-ray absorption contrast with its period being the same as that of the self image of the first grating, wherein the second grating is preferably placed closely in front of the detector with its lines parallel to those of first line grating.

Typical arrangement for the near-field-regime and the Talbot regime are given hereinafter. For the near-field-regime operation, the distance between the first and the second grating may be chosen freely within the regime, and for the Talbot-regime may be chosen according to $$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda},$$

where n=1, 3, 5, . . . and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases},$$

where l=1, 2, 3, . . . , $D_n$ is an odd fractional Talbot distance when the parallel X-ray beam is used, while $D_{n,sph}$ is that when the fan or cone X-ray beam is used, L is the distance between the source and the first grating.

In order to realize a phase stepping approach, the phase stepping may be performed by mechanical shift of one grating with respect to the other(s).

A suitable grating structure can be achieved when the grating structure is manufactured by planar technology according to the method claimed in the European Patent Application 10167569.2. The differential phase information can be suitably obtained according to the method claimed in the European Patent Application 10167569.2. The phase relation between the first grating and the second grating corresponds exactly to the value for which the intensity curve is expanded by a first order Taylor series and the differential phase information is obtained according to the method claimed in the International Patent Application WO 2010/089319 A1.

In a preferred example, the PCA fused image can be calculated by the multiplication of the first principal component and the data matrix $$I\_e_1 = e_1^T \cdot I = s_1 \times I_{AC} + s_2 \times I_{DFI},$$

where; $e_1 = [s_1, s_2]^T$.

Advantageously, the PCA fused image may be generated by performing PCA on the vector images for the absorption dominated pixels and for the differential phase dominated pixels and for the dark field dominated pixels. Therefore, the fused image already contains after the first PCA operation all the beneficial components of the three different pixel types.

A preferred embodiment for the merging is achievable when the differential phase dominated pixels are merged into the PCA fused image to achieve edge enhancement effect by spatial space operation, Fourier space operation or other image fusion schemes. Another preferred method to merge the differential phase dominated pixels is achieved when one spatial space way to merge the differential phase dominated pixels into the PCA fused image is given by $$I_{fuse} = I\_e_1 + \delta \times |I_{DPC}|,$$

where the scale value $\delta$ controls how strong the edge enhancement effect is.

At this stage, it has to be mentioned that the present invention alternatively also is deductable when the absorption, the differential phase contrast and the darkfield signals are provided by alternative methods different from gratings.

In the field of the medical imaging and the interpretation of the images, the invention provides for a freedom whether to fusion the absorption dominated pixels and the differential phase dominated pixels and the dark field dominated pixels prior or after 3D reconstruction of the gathered 2D images.

Therefore, 3d reconstructions are available benefiting from the positive effects of the image fusion.

Further advantageous features are listed in the remaining dependent claims.

Preferred embodiments are hereinafter explained more detailed with respect to the attached drawing which depicts in:

DESCRIPTION OF THE INVENTION

Figure 1:
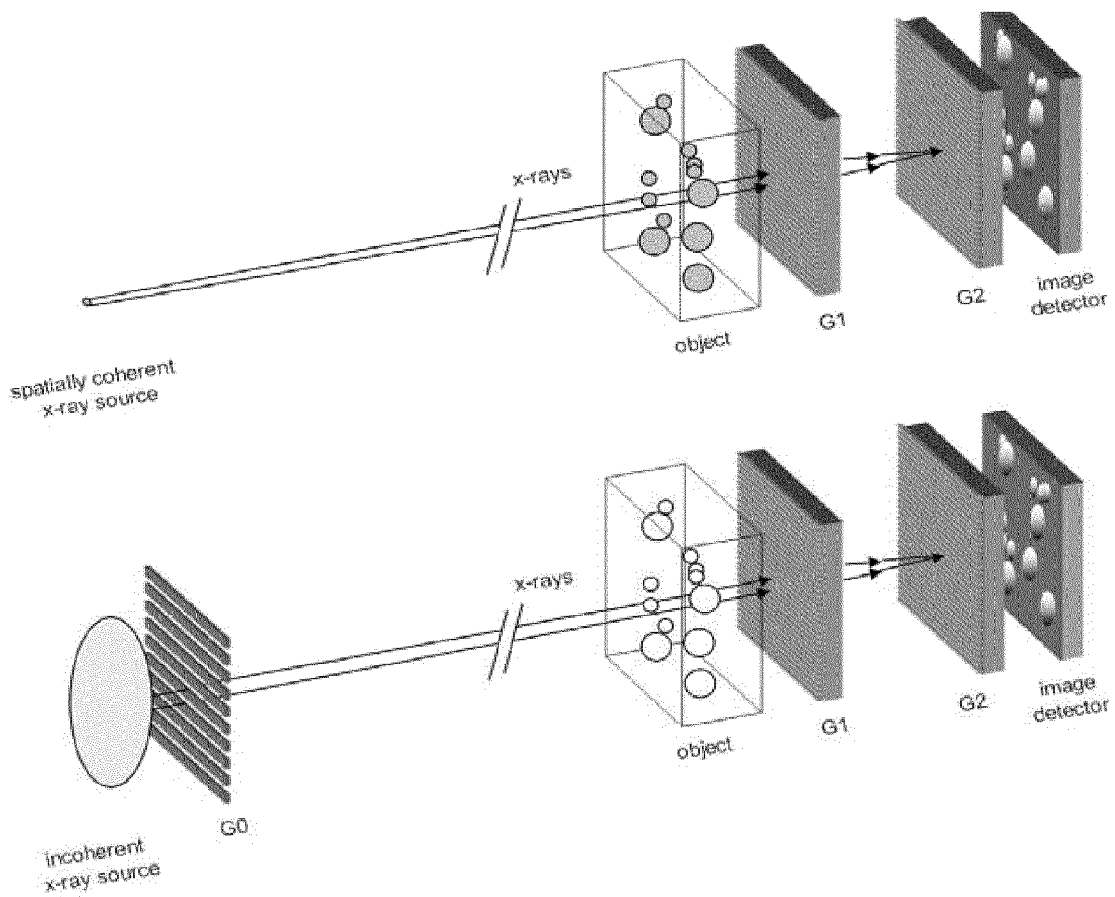
FIG. 1 illustrates schematically a two-grating set-up (top) and a three grating set-up (bottom) for phase contrast x-ray imaging.

It has been shown that RGB (red-green-blue) or IHS (intensity-hue-saturation) colour coding image fusion methods are an efficient and intuitive way to represent the three physical (AC, DPC, DFI) signals and are well suited to human vision [13]. However, such approaches do not comply with conventional gray-level images in modern radiology. Therefore, new strategies and algorithms to best merge different physical signals with improved diagnostic contents have been developed according to the present invention. The present invention proposes an image fusion scheme for differential phase contrast imaging according to the following steps:

Step 1

Hereafter, images are represented as column vectors. An image I is obtained from the column-wise extraction of pixel values in a medical 2D image f $$f(x,y) = I(y*n+x)$$

where m×n is the image size. The size of an image vector is N×1 with N=m*n. $I_{AC}$, $I_{DPC}$, $I_{DFI}$ and $I_{Phase}$ represent the absorption, differential phase contrast, scattering and phase images, respectively.

Step 2 (Optionally)

Before starting with the image fusion, DPC and DFI images can be filtered (either low pass filter, non-linear kernels or similars) to cope with the intrinsically lower signal-to-noise ratio compared to AC images.

Step 3

In this step, the AC image and the DFI image are fused by Principal Component Analysis (PCA). Considering the similarities of the AC and DFI images (since scattering always occurs when absorption is strong), the PCA is adopted to grasp the most relevant (eventually even complementary) information from both AC and DFI images. Redundant contributions are automatically discarded.

The actual computation of the PCA is a well-defined mathematical operation. Assume a collection of M data samples $I_i$ with i=1, ..., M. Each data sample $$I_i = (x_1, x_2, \ldots, x_N)^\tau$$

is a vector of dimension N. The first action is to subtract the mean of each data sample from $I_i$, $$\mathrm{Mean}_{I_i} = \frac{1}{N}\sum x_j, j=1, \ldots, N$$

so that each sample has a zero mean. The new data samples are noted as $I_i'$. Then compute the covariance matrix Cov of the data matrix $I = [I_1', I_2', \ldots, I_M']$ by $$\mathrm{Cov} = \frac{1}{N} I^T \times I$$

The size of the covariance matrix is equal to M×M and is independent from the dimension of each data sample N. Then, the eigenvector matrix $E = [e_1, e_2, \ldots, e_M]$ is computed where each eigenvector $e_i$ has the same dimension as the data samples M and the eigenvalues $[v_1, v_2, \ldots, v_M]$ of the covariance matrix by $$\mathrm{Cov} = E^T \times V \times E$$

where V is a diagonal matrix with all the eigenvalues on the diagonal $$V = \begin{bmatrix} v_1 & 0 & \ldots & 0 \\ 0 & v_2 & \ldots & 0 \\ \vdots & \vdots & \vdots & \vdots \\ 0 & 0 & \ldots & v_M \end{bmatrix}$$

The eigenvector corresponding to the largest eigenvalue is called the first principal component. Along the direction of this vector, the data set has maximum variance (that is, accounts for as much of the variability in the data as possible).

A feature vector which contains most of the information is defined by $$I_{feature} = e_1^T \cdot I$$

if it is assumed that $v_1$ is the largest eigenvalue of that matrix. $I_{feature}$ is then a linear combination of the data set I.

Specifically, to fuse the AC image and the DFI image, the data matrix is $I = [I'_{AC}, I'_{DFI}]$, where $I'_{AC}$ and $I'_{DFI}$ represent the AC and DFI images with subtracting mean, respectively.

The covariance matrix of the two images can be calculated by $$\mathrm{Cov} = \frac{1}{N} I^T \times I = \begin{pmatrix} \rho_{11} & \rho_{12} \\ \rho_{21} & \rho_{22} \end{pmatrix},$$

where Cov is a 2×2 matrix. Therefore, two eigenvalues $v_1$, $v_2$ and their corresponding eigenvector are obtained:

$$e_1 = [s_1, s_2]^\tau \text{ and } e_2 = [t_1, t_2]^\tau.$$

Without loss of generality, it is assumed that $v_1 > v_2$. The eigenvector $v_1$ then represents the principal component of the data set.

Two new images can be obtained by projecting the dataset to the directions decided by $e_1$ and $e_2$:

$$I\_e_1 = e_1^T \cdot I = s_1 \times I_{AC} + s_2 \times I_{DFI}$$

$$I\_e_2 = e_2^T \cdot I = t_1 \times I_{AC} + t_2 \times I_{DFI}$$

I_e$_1$ is regarded as the AC and DFI fused image. An example for this fused AC and DFI image is shown in FIGS. 2b) and e).

The PCA fusion method normally requires the underlying images to be rather similar. Obviously, the DPC image does not match this criteria and has to be merged into the final image according to another approach, as suggested in the next steps.

Step 4

Here it is worth mentioning that the phase image can be obtained from the DPC signal by image processing. It is also possible to run the PCA fusion method on AC, Phase and DFI images by using a data matrix I=[I$_{AC}$, I$_{Phase}$, I$_{DFI}$], as disclosed in Step 3 for the AC and DFI images.

Figure 2:
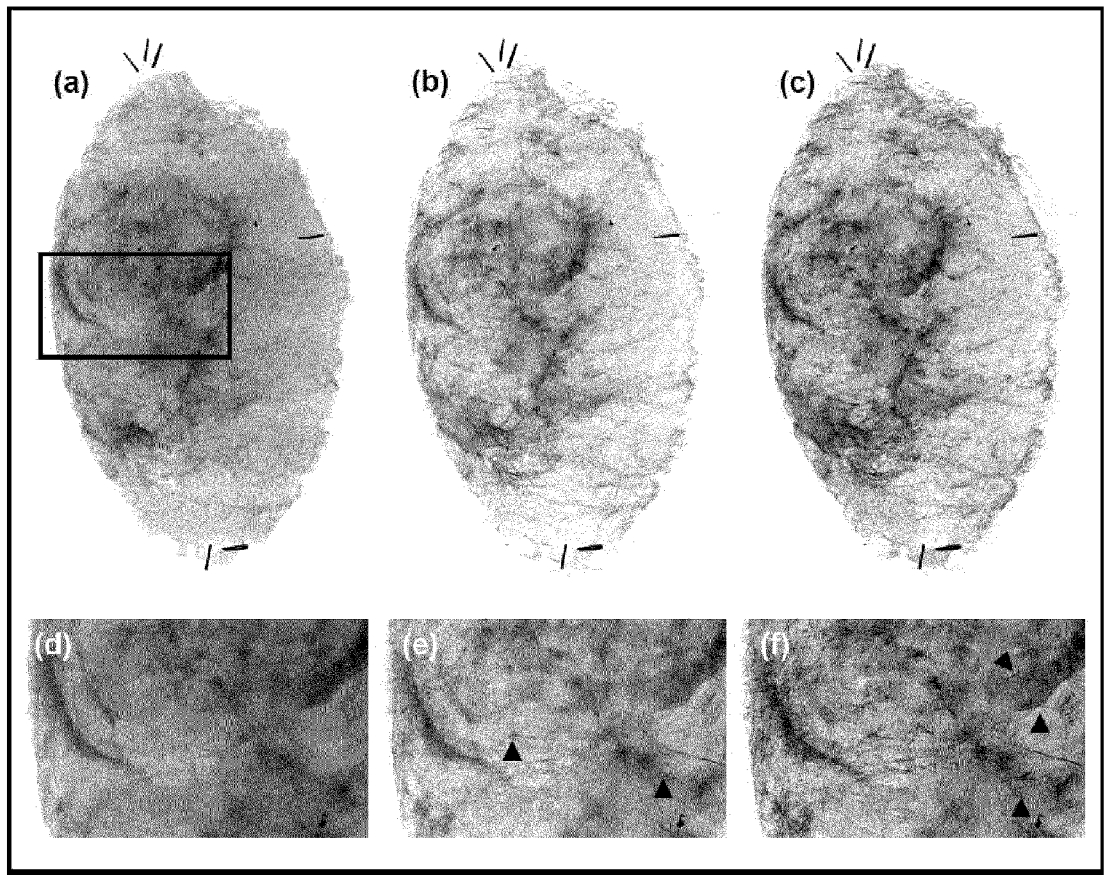
FIG. 2 shows results of the fusion scheme, tested on a human breast, wherein a) is a conventional mammogram of AC signals, b) is the PCA fused image of the AC and DFI signals, and c) is the final fused image by merging the PCA fused image with the DPC signals; d) to f) correspond to the ROI (inset in (a)) in a) to c), respectively; e) shows clear detailed features as indicated by arrows; furthermore, arrows in f) show the edge enhancement benefits clearly.

From the point of view of image processing, the DPC signal represents the edge information of the sample. Phase contrast imaging has large values where the probe characteristics show certain utterly local changes in the behaviour of x-ray absorption. Accordingly, the signals are high at such edges where the phase shift changes the most. It can be considered as a complementary information, which can be merged the PCA fused image by either spatial space methods, Fourier space methods (which adds the high frequency components of the DPC signals to the I_e$_1$ signal) or other image fusion schemes. In the present example, a possible and (very simple) approach is suggested, and is defined by:

$$I_{fuse} = I\_e_1 + \delta \times |I_{DPC}|$$

where the scale value δ controls how strong the edge enhancement effect is developed in the final fused image I$_{fuse}$. An example for the superior quality of the final fused image is shown in FIG. 2 which shows results of the fusion scheme proposed in this invention for the x-ray images of a human breast. Part (a) in FIG. 2 shows the conventional mammogram (AC signal) as this image is taken by a standard x-ray tube set-up. Part (b) already shows the PCA fused image of AC and DFI and Part (c) represents the final fused image by merging the PCA fused image and the DPC image. Parts (d) to (f) correspond to the ROI (box inset in (a)) in Parts (a) to (c), respectively. Part (e) already shows clear detailed features as indicated by the arrows which are not apparent from Part (d). Furthermore, the arrows in Part (f) show the edge enhancement benefits clearly.

Therefore, the final fused image I$_{fuse}$ contains information from the three different physical quantities. The redundant information in AC and DFI images is reduced by the PCA and the edges are enhanced by the DPC image. Of course, the final fused image can be further post-processed by conventional image analysis algorithms to achieve better contrast enhancement in specific fields.

At this stages, it has to be emphasized that this image fusion method can also be used to pre/post-process data prior/after 3D reconstruction, i.e. for computed tomographic application or ultra-sonic applications.

The invention claimed is:

1. A method for image fusion based on Principal Component Analysis for differential phase contrast imaging merging absorption signals, differential phase signals, and dark-field signals, the method comprising the steps of:
   a) gathering a series of 2D images, each of the 2D images containing absorption dominated pixel and/or differential phase dominated pixel and/or dark field dominated signals;
   b) obtaining a vector image by a column-wise extraction of pixel values for each of the absorption dominated pixels and the differential phase dominated pixels and the dark field dominated pixels;
   c) fusing the vector images of the absorption dominated pixels and the dark-field dominated pixels by a principal component analysis in order to generate PCA fused images; and
   d) merging the vector images of the differential phase dominated pixels into corresponding PCA fused images by a suitable image fusion scheme.

2. The method according to claim 1, which comprises selecting the image fusion scheme from the group consisting of a spatial space methods, a Fourier space method, and PCA.

3. The method according to claim 1, wherein the differential data are data obtained from an x-ray system (in particular hard x-rays) for obtaining quantitative x-ray images from a sample, the system comprising:
   a) an X-ray source;
   b) at least a first grating and a second grating;
   c) a position-sensitive detector with spatially modulated detection sensitivity having a number of individual pixels;
   d) a recording device for recording images of the detector;
   e) an evaluation device for evaluating the intensities for each pixel in a series of images in order to identify a characteristic of the object for each individual pixel as an absorption dominated pixel and/or a differential phase contrast dominated pixel and/or an x-ray scattering dominated pixel; and the method further comprising:
   f) collecting the series of images by continuously or stepwise rotating from 0 to π or 2π, in radians, either the sample or the X-ray system with the source relative to the sample.

4. The method according to claim 1, operated either in the near field regime or in the Talbot-regime.

5. The method according to claim 1, wherein said first grating is a line grating configured either as an absorption grating or a phase grating which is a low absorption grating but generating a considerable X-ray phase shift (shifted by n or odd multiples thereof).

6. The method according to claim 1, wherein said second grating is a line grating having a high X-ray absorption contrast with a period thereof being equal to a self image of the first grating, and the method comprises placing the second grating in close vicinity in front of the detector with lines thereof parallel to lines of the first line grating.

7. The method according to claim 1, which comprises, for near-field-regime operation, choosing a distance between the first and second gratings freely within the regime, and for Talbot-regime operation, choosing the spacing distance according to:

$$D_{n,sph} = \frac{L \cdot D_n}{L - D_n} = \frac{L \cdot n \cdot p_1^2 / 2\eta^2 \lambda}{L - n \cdot p_1^2 / 2\eta^2 \lambda}$$

where n=1, 3, 5, . . . and $$\eta = \begin{cases} 1 & \text{if the phase shift of } G_1 \text{ is } (2l-1)\frac{\pi}{2}, \quad p_2 = \frac{L + D_{n,sph}}{L} p_1 \\ 2 & \text{if the phase shift of } G_1 \text{ is } (2l-1)\pi, \quad p_2 = \frac{L + D_{n,sph}}{L} \frac{p_1}{2} \end{cases}$$

where: l=1, 2, 3, . . . ,
   $D_n$ is an odd fractional Talbot distance when a parallel X-ray beam is used, while $D_{n,sph}$ is the Talbot distance when a fan or cone X-ray beam is used, and
   L is the distance between the source and the first grating.

8. The method according to claim 1, wherein phase stepping is performed by mechanical shift of one grating with respect to the other.

9. The method according to claim 1, wherein the grating structure is a grating structure manufactured by planar technology according to the method of application Ser. No. 13/807,537.

10. The method according to claim 1, wherein the differential phase information is obtained according to the method of application Ser. No. 13/807,537.

11. The method according to claim 1, wherein the phase relation between the first grating and the second grating corresponds exactly to a value for which the intensity curve is expanded by a first order Taylor series and the differential phase information is obtained according to the method of patent application publication US 2012/0041679 A1.

12. The method according to claim 1, which comprises calculating the PCA fused image by a multiplication of a first principal component and the data matrix where $$I\_e_1 = e_1^T \cdot I = s_1 \times I_{AC} + s_2 \times I_{DFI}$$

where $e_1 = [s_1, s_2]^T$.

13. The method according to claim 1, which comprises generating the PCA fused image by performing PCA on the vector images for the absorption dominated pixels and for the differential phase dominated pixels and for the dark field dominated pixels.

14. The method according to claim 1, which comprises merging the differential phase dominated pixels into the PCA fused image to achieve edge enhancement effect by spatial space operation, Fourier space operation or a further image fusion scheme.

15. The method according to claim 1, which comprises merging the differential phase dominated pixels into the PCA fused image by setting $$I_{fuse} = I\_e_1 + \delta \times |I_{DPC}|$$

where the scale value $\delta$ controls how strong the edge enhancement effect is.

16. The method according to claim 1, which comprises providing absorption, differential phase contrast and dark field signals by alternative methods different from gratings.

17. The method according to claim 1, which comprises fusing the absorption dominated pixels and the differential phase dominated pixels and the dark field dominated pixels prior or after 3D reconstruction of the 2D images.

* * * * *